(12) United States Patent
Bailly et al.

(10) Patent No.: US 7,662,087 B2
(45) Date of Patent: Feb. 16, 2010

(54) GASTRIC RING FOR TREATMENT OF OBESITY

(75) Inventors: Pierre Bailly, Caluire (FR); Michel Therin, Lyons (FR)

(73) Assignee: Sofradim Production, Trevoux (FR)

(*) Notice: Subject to any disclaimer, the term of this patent is extended or adjusted under 35 U.S.C. 154(b) by 460 days.

(21) Appl. No.: 10/499,679

(22) PCT Filed: Jan. 8, 2003

(86) PCT No.: PCT/FR03/00040

§ 371 (c)(1),
(2), (4) Date: Aug. 10, 2004

(87) PCT Pub. No.: WO03/057092

PCT Pub. Date: Jul. 17, 2003

(65) Prior Publication Data

US 2005/0038458 A1 Feb. 17, 2005

(30) Foreign Application Priority Data

Jan. 9, 2002 (FR) .................................. 02 00261

(51) Int. Cl.
*A61F 2/00* (2006.01)
(52) U.S. Cl. ........................................ 600/37; 606/157
(58) Field of Classification Search .................. 600/37; 606/139, 151, 157; 128/912; 49/142
See application file for complete search history.

(56) References Cited

U.S. PATENT DOCUMENTS

| 4,271,827 | A | * | 6/1981 | Angelchik | 600/37 |
| 5,707,378 | A | * | 1/1998 | Ahn et al. | 606/139 |
| 5,713,912 | A | * | 2/1998 | Porter | 606/158 |
| 5,919,233 | A | * | 7/1999 | Knopf et al. | 128/898 |
| 6,273,852 | B1 | * | 8/2001 | Lehe et al. | 600/30 |
| 6,814,716 | B2 | * | 11/2004 | Bouphavichith et al. | 604/174 |
| 7,025,063 | B2 | * | 4/2006 | Snitkin et al. | 128/885 |
| 2002/0072759 | A1 | * | 6/2002 | Fry | 606/157 |
| 2004/0133219 | A1 | * | 7/2004 | Forsell | 606/151 |
| 2004/0267291 | A1 | * | 12/2004 | Byrum et al. | 606/157 |
| 2005/0125014 | A1 | * | 6/2005 | Duluco et al. | 606/151 |

FOREIGN PATENT DOCUMENTS

| EP | 0 263 360 A2 | 4/1988 |
| EP | 0 531 742 A1 | 3/1993 |
| EP | 0 611 561 A1 | 8/1994 |
| WO | WO 86/04498 | 8/1986 |

* cited by examiner

*Primary Examiner*—John P Lacyk
(74) *Attorney, Agent, or Firm*—Carter, DeLuca, Farrell & Schmidt, LLP

(57) ABSTRACT

This gastric ring (1) comprises:
 a band (3) which is able to surround the wall of the stomach, and
 connection means (4, 40, 51, 54) with which this band can be maintained in the form of a ring.

According to the invention, the band (3) is made of a bioabsorbable material.

24 Claims, 3 Drawing Sheets

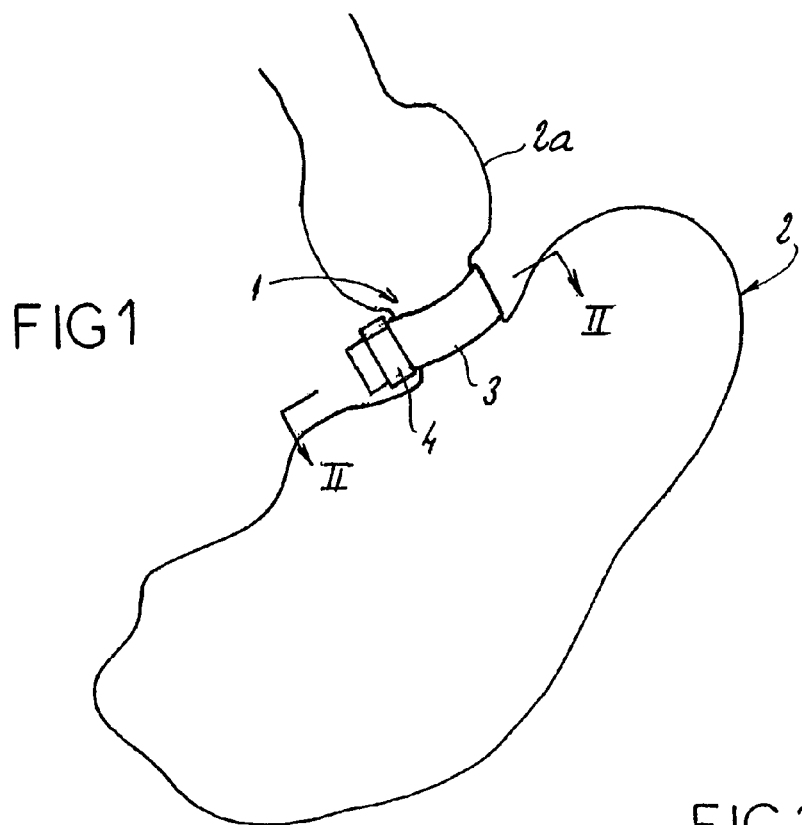
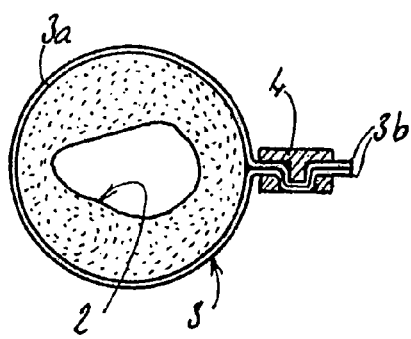
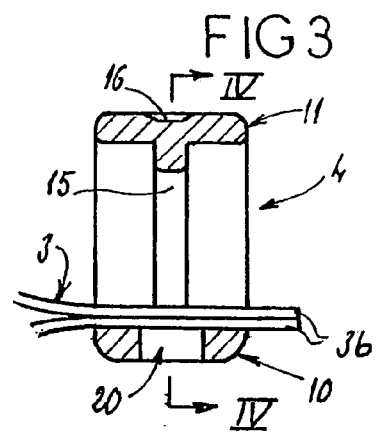

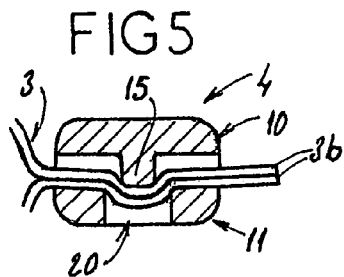
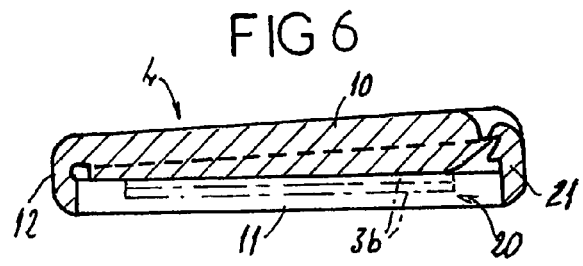
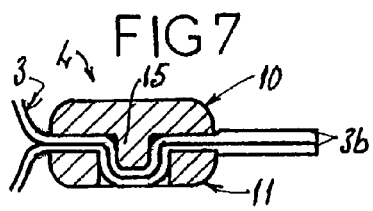
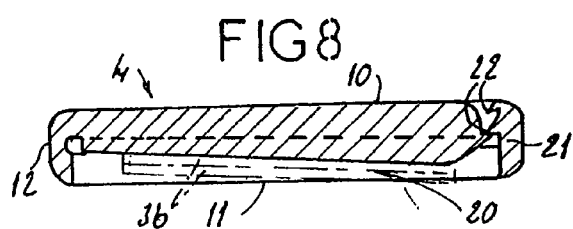
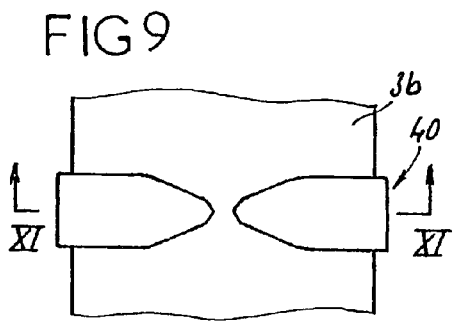
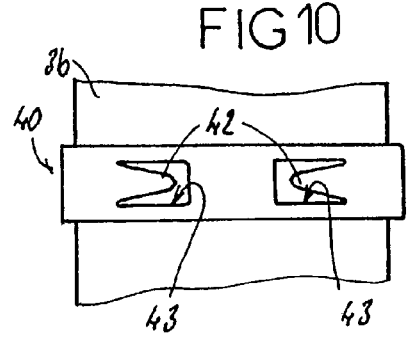
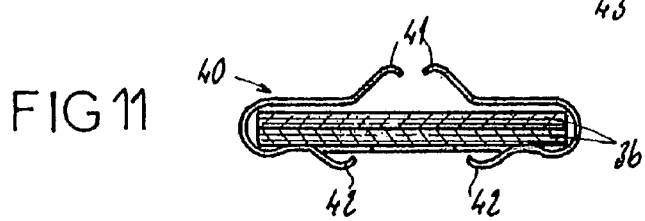
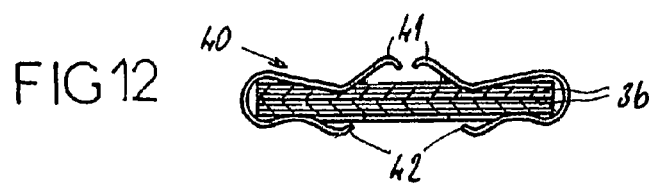
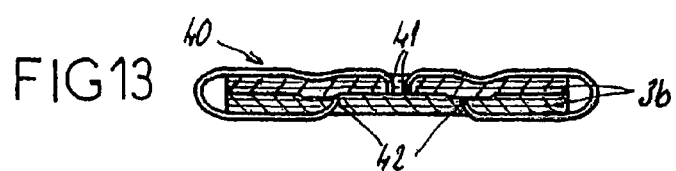

GASTRIC RING FOR TREATMENT OF OBESITY

The present invention concerns a gastric ring for treatment of obesity. Such a ring is also presently known as a "gastroplasty ring".

It is known to treat a patient with pathological obesity by fitting a ring round the patient's stomach in such a way as to create, in the upper part of the stomach, a pouch of small dimensions, and an opening for flow of food, also of small dimensions.

The principle of such rings is well known, and the documents WO-A-86/04498 and EP-A-0 611 561 may be cited as documents illustrating existing gastric rings.

Some of the existing rings have the disadvantage of being relatively aggressive with regard to the wall of the stomach, to the point of causing inflammation of this wall, or, in extreme cases, perforations of this wall. This aggressiveness is the result of the solid and rigid nature of this ring and of the presence of an inflatable pouch situated on the internal face of the ring, this inflatable pouch making it possible to adjust the surface area of the opening delimited by the ring, by exerting on the stomach wall a pressure directed radially inward.

The implantable chambers permitting percutaneous inflation or deflation of these inflatable pouches, and the tubes connecting these chambers and these pouches, have the disadvantage of posing risks of leakage, migration and infection.

The existing rings also have the disadvantage of posing risks of tilting or sliding called "slippage" and of requiring follow-up operations when it is necessary to replace them or withdraw them after a certain period of treatment.

It is an object of the present invention to overcome all these disadvantages of the existing devices by arrangements or means which can be used in combination with one another.

The ring to which the invention relates comprises in a manner known per se:
  a band which is able to form a ring round the wall of the stomach, and
  connecting means with which this band can be maintained in the form of said ring.

According to a first solution, the band is made of at least one bioabsorbable or biodegradable material and comprises a face intended to come into contact with the wall of the stomach.

"Biodegradable" or "bioabsorbable" signifies the property by which a material degrades in vivo by a cellular, enzymatic or microbial mechanism (cf. for example degradation of collagen by collagenase) or by a physical-chemical mechanism (cf. for example hydrolysis of a lactic acid polymer).

Such a bioabsorbable material is preferably chosen from the group consisting of polymers of p-dioxanone, polyglycolides, polyorthoesters, polymers of trimethylene carbonate, stereocopolymers of L and D lactic acid, homopolymers of L lactic acid, copolymers of lactic acid and a compatible comonomer, such as alphahydroxy acid derivatives. Still more preferred, the bioabsorbable material has a polydispersity of less than 2.

By way of a preferred example, the biodegradable or bioabsorbable material is a lactic acid polymer (PLA) or polyglycolic acid polymer (PGA), or a copolymer of lactic acid or polyglycolic acid (PLA-PGA).

The band preferably comprises or is made of at least one bioabsorbable material.

The bioabsorbability of the band eliminates the need for removing the ring and thus for having to reoperate on the patient for this purpose. Moreover, and above all, the fibrosis which forms naturally round this band is preserved and remains after complete absorption of the band, this fibrosis generating scar contraction of the stomach wall, which means there is no need to use an inflatable pouch to adjust the cross section of the opening of the ring.

The gradual tissue integration of the band secures the ring to the stomach wall and completely prevents migration ("slippage") of the ring and produces a wide surface area of contact between tissues and band, thus promoting absorption of the latter.

The band can be formed by a lactic or polyglycolic acid polymer, or by a copolymer of lactic or polyglycolic acid.

These materials have a kinetic of absorption of several months, or even several years, so as to maintain the effect of the band for a period sufficient to significantly reduce the body mass index.

The band according to the invention can be obtained by any suitable technique, in particular by molding or extrusion of its constituent material, for example thermoplastic.

At least the face of the band intended to come into contact with the stomach wall preferably comprises a smooth coating able to separate this face and this wall at least temporarily.

This coating makes it possible to prevent or delay direct contact between the band and the stomach wall until the time when the most inflammatory phases of cicatrization of this wall have elapsed. The aforementioned tissue integration is thus separate in time from the cicatrization of the initial lesions generated by the fitting of the ring, which thus limits the risk of erosion of the stomach wall.

This coating can be a bioabsorbable material, in particular a crosslinked collagen material.

According to a second configuration, the band can have a thickness which is such that it has a flexibility allowing it to be curved transversely with respect to its longitudinal direction. In this case, said connection means of the ring according to the invention can include two lateral portions of the band which prolong the central portion of the band intended to surround the patient's stomach, and they can be conformed for placing said lateral portions of the band in a substantially radial direction with respect to the circle formed by the central portion of the band when the ring is placed on a patient's stomach, these lateral portions projecting outward from this circle.

The gastric ring does not therefore involve one of these lateral portions overlapping the other, such overlapping leading, in some devices of the prior art, to an overthickness being created at the radially inner face of the circle, which is aggressive to the wall of the stomach.

According to one possible embodiment of the invention, said connection means include at least one fastener comprising movable parts which can engage with said lateral portions of the band.

Advantageously, in this case, said movable parts are displaceable between two positions, namely a position of sliding, in which the fastener can slide along said lateral portions, and a position of locking of said lateral portions, in which all possibility of sliding of the fastener relative to these lateral portions is prevented.

The sliding of the fastener along said lateral portions makes it possible to adjust the tightening of the band round the stomach.

Said lateral portions of the band can then have a length greater than that which is necessary for engagement of the fastener on these, this length being such that the fastener can be slid along these lateral portions until the desired cross section is obtained for the opening delimited by the ring, and can then be brought to the position of locking of these lateral portions.

The fastener can comprise means for immobilizing said movable parts in the aforementioned respective positions of sliding and of locking, preferably of the irreversible snap-fit type.

The fastener can comprise or be made of a bioabsorbable or biodegradable material. It can include a radiopaque substance of the barium sulfate type when it is not made of a naturally radiopaque material.

According to one possibility, the fastener comprises two movable parts which are dimensioned to surround said lateral portions of the band and to hold these portions clamped against one another, these movable parts being connected to one another at one of their longitudinal ends by means of a film hinge.

This film hinge can be shaped in such a way as to hold said movable parts normally in a position in which one movable part is at a distance from the other, in order to facilitate engagement of the fastener on said lateral portions of the band.

One of said movable parts can comprise at least one rib protruding from its face directed toward the other movable part, this other movable part then having a slot in which the rib or ribs are intended to be engaged.

According to another possibility, the fastener is made of a non-elastically deformable material, for example a metal, and comprises deformable tabs which, in a position of deformation, are able to penetrate into the material forming said lateral portions of the band and thereby ensure fixation of these lateral portions with respect to one another.

Such a fastener made of a metal has the advantage of not taking up much space.

According to a third configuration, the band of the ring according to the invention can also have a thickness such that it has a rigidity preventing its being curved transversely with respect to its longitudinal direction.

In this case, the band can be made up of at least two parts connected pivotably to one another, making it possible to place this band in an elongate shape such that this band can be introduced into the patient's body by minimally invasive surgical techniques such as celioscopy or laparoscopy.

The band can in particular comprise a plurality of "links" connected pivotably to one another.

Said connection means of the ring according to the invention can then comprise a tab having at least one catch and being able to be engaged in a corresponding cavity into which there protrudes at least one catch complementing that of the tab, said catch of the tab being able to extend beyond the catch of the cavity upon engagement of the tab in the cavity and to be locked behind it to ensure connection of the two ends of the band to one another.

To ensure that it is clearly understood, the invention is again described below with reference to the attached diagrammatic drawing which shows, by way of nonlimiting examples, three possible embodiments of the gastric ring to which the invention relates.

To simplify matters, the elements or parts of elements found from one embodiment to another are designated by the same reference numbers.

FIG. 1 is a perspective view of a gastric ring according to a first embodiment, when it is in place on a patient's stomach;

FIG. 2 is a cross section along the line II-II in FIG. 1;

FIG. 3 is a view, on an enlarged scale, of a fastener which it comprises, in a cross section along the line III-III in FIG. 4, and in the open position of this fastener;

FIG. 4 is a view of the fastener in cross section along the line IV-IV in FIG. 3;

FIG. 5 is a view of the fastener similar to FIG. 3, in a position of partial closure of this fastener, permitting sliding of this fastener relative to lateral portions of a band comprised by the ring;

FIG. 6 is a view of the fastener similar to FIG. 4, in this same position of partial closure;

FIG. 7 is a view of the fastener similar to FIG. 3, in a position of complete closure of this fastener, preventing any possibility of the fastener sliding relative to the lateral portions of said band;

FIG. 8 is a view of the fastener similar to FIG. 4, in this same position of complete closure;

FIG. 9 is a side view of the aforementioned fastener, according to a second embodiment;

FIG. 10 is a view of this fastener in a direction opposite to that according to FIG. 9;

FIG. 11 is a view of this fastener in cross section along the line XI-XI in FIG. 9, the fastener being in the open position;

FIG. 12 is a view of the fastener similar to FIG. 11, the fastener being in the partially closed position;

FIG. 13 is a view of the fastener similar to FIG. 11, the fastener being in the completely closed position;

FIG. 1 shows a gastric ring 1 for treatment of pathological obesity of a patient, placed on the stomach 2 of this patient.

Figure 14:
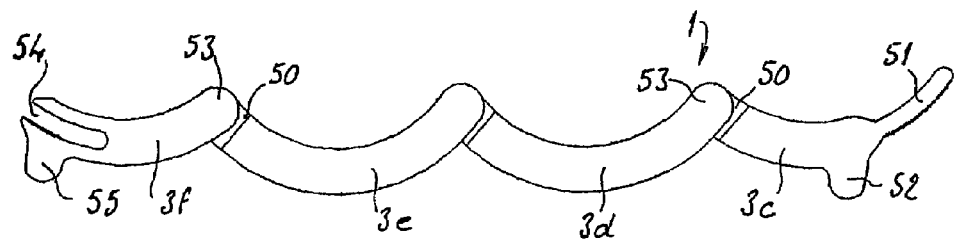
FIG. 14 is a side view of the ring according to a third embodiment, before closure.

This ring 1 comprises a band 3 and a fastener 4 able to maintain the band 3 around the stomach 2, in order to create, in the upper part of the stomach, a pouch 2a of small dimensions and a distal opening for flow of food, also of small dimensions.

In this embodiment of the ring, the band 3 is of such a thickness that it has a flexibility allowing it to be curved transversely with respect to its longitudinal direction; as FIG. 2 shows, it defines a central portion 3a able to surround the wall of the stomach 2 in a circular trajectory, and two lateral portions 3b able to be connected to one another by means of the fastener 4, in order to maintain the band 3 round the stomach 2.

The portions 3b have a length much greater than that which is necessary for the fastener 4 to engage on them. They thus permit easy manipulation of the band 3, and in particular its passage behind the stomach.

The band 3 is made of a bioabsorbable or biodegradable material, such as a lactic or polyglycolic acid polymer, or a lactic or polyglycolic acid copolymer, and has been obtained by molding or extrusion.

Referring to FIGS. 3 to 8, it will be seen that the fastener 4 comprises two movable parts 10, 11 which are dimensioned to surround the lateral portions 3b of the band 3 and hold these portions 3b clamped against one another in a substantially radial direction with respect to the circle which the central portion 3a forms, as is shown in FIG. 2, these lateral portions 3b protruding outward from this circle.

The movable parts 10, 11 are connected to one another at one of their longitudinal ends, by means of a film hinge 12. This film hinge 12, in the nondeformed state, holds the parts 10, 11 in the position shown in FIGS. 3 and 4, in which the part 10 is a distance away from the part 11. This spacing apart facilitates engagement of the fastener 4 on the portions 3b, particularly when this fastener 4 is put in place using minimally invasive techniques such as celioscopy or laparoscopy. The film hinge 12 can be deformed to allow the part 10 to come to the positions of partial closure and complete closure of the fastener 4, shown in FIGS. 5 and 6 and FIGS. 7 and 8, respectively.

The part 10 comprises a rib 15 protruding from its face directed toward the part 11, and a median notch 16 formed in its lateral end edge, at the end opposite from the hinge 12. In the area of the bottom of the notch 16, the rib 15 forms a snap-fit catch 17, that is to say a projection having an inclined wall at the side toward the part 11 and a plane locking wall at the side opposite from this part 11.

The part 11 has a central slot 20 in which the rib 15 is intended to be engaged, as is shown in FIGS. 7 and 8. At the end opposite from the hinge 12, this part 11 comprises a central tooth 21 which can be engaged in the notch 16 and which is equipped with two stepped snap-in catches 22. These catches 22 are able to cooperate with the catch 17, as shown respectively in FIGS. 6 and 8.

As will be appreciated with reference to FIGS. 3 to 8, these catches 17 and 22 form irreversible snap-fit means with which it is possible to lock said movable parts 10, 11 with respect to one another in two positions, namely:

a position in which the lateral portions 3b are not clamped, as is shown in FIGS. 5 and 6, in which these two portions 3b can slide with friction between the rib 15 and the portions of part 11 which longitudinally delimit the slot 20; and a position in which these lateral portions 3b are locked, as is shown in FIGS. 7 and 8, in which any possibility of sliding of these portions 3b is prevented on account of these portions 3b being clamped between the rib 15 and said portions of part 11 which longitudinally delimit the slot 20.

The fastener 4 can thus be placed on the portions 3b when it is in the open position, can be brought to the non-clamped position by simply pressing the part 10 in the direction of the part 11 so as to bring the catch 17 into engagement with the upper catch 22, can be slid along these portions 3b until the desired cross section is obtained for the admission opening for food into the stomach 2, and can be brought to the locked position by simply pressing the part 10 in the direction of the part 11 in such a way as to bring the catch 17 into engagement with the lower catch 22. The excess parts of the portions 3b can then be cut off.

FIGS. 9 to 13 show a fastener 40 according to a second embodiment, formed by folding a metal band into a C shape so as to delimit a conduit in which the portions 3b can be engaged.

This fastener 40 comprises, at one end, two curved tabs 41 formed in the ends of said metal band and, at the opposite end, two curved tabs 42 individualized by suitable cutouts 43 from this same metal band. The tabs 41 are able to penetrate into one of the portions 3b, while the tabs 42 are able to penetrate into the other portion 3b.

As is shown in FIG. 12, the fastener 40 can be deformed outside the tabs 41, 42 in order to obtain a possibility of sliding of the portions 3b with friction in the fastener 40.

FIG. 13 shows that this same fastener 40 can be deformed in the area of the tabs 41, 42 so that these tabs 41, 42 penetrate into the portions 3b so as to block any possibility of sliding of these portions 3b in the fastener 40.

Figure 15:
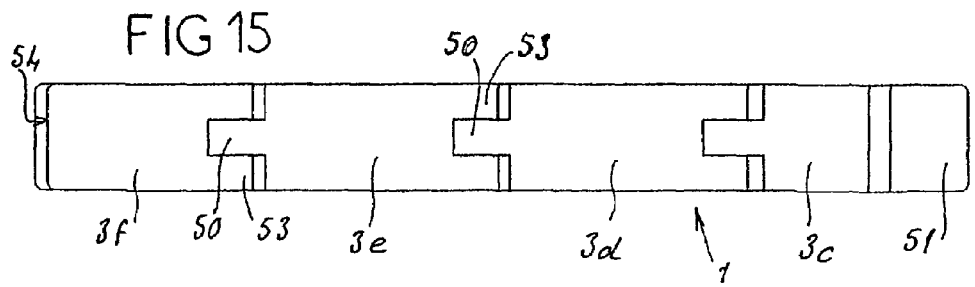
FIG. 15 is a plan view thereof.
Figure 16:
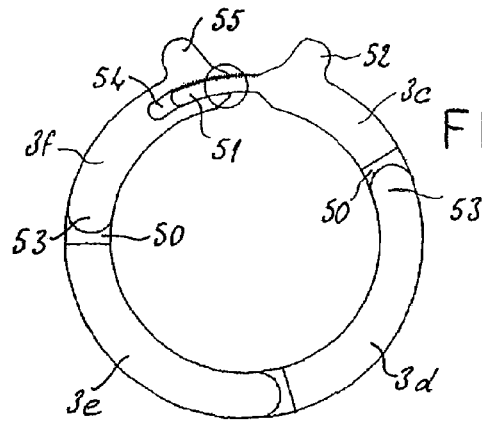
FIG. 16 is a side view thereof, after closure.

FIGS. 14 to 16 show a ring 1 according to another embodiment, in which the band 3 is of such a thickness that it has a rigidity preventing its from being curved transversely with respect to its longitudinal direction.

The band 3 in this case comprises four "links" 3c, 3d, 3e, 3f connected pivotably to one another, which make it possible to place this band 3 in the elongate form shown in FIGS. 14 and 15. This elongate form is such that the band 3 can be introduced into the patient's body by minimally invasive surgical techniques such as celioscopy or laparoscopy.

The link 3c situated at one end of the band 3 comprises, at one end, a stub 50 allowing it to be joined, with possible pivoting, to the adjacent link 3d, and, at its other end, a curved tab 51 comprising a plurality of toothed catches. On its convex face and near the tab 51, the link 3c has a boss 52.

At its end directed toward the link 3c, the link 3d comprises two tabs 53 forming a skirt for receiving the stub 50 and, at its other end, a stub 50 identical to that of the link 3c. The connection of tabs 53 and stub 50 is obtained by means of a pin (not shown).

The link 3e comprises tabs 53 and a stub 50 identical to those of the link 3d.

The link 3f situated at the other end of the band 3 comprises, at one end, tabs 53 identical to those of the link 3d, and, at its other end, a cavity 54 of a shape corresponding to that of the tab 51, into which there project a plurality of toothed catches complementing those of the tab 51. On its convex face and at an end of the zone delimiting the cavity 54, the link 3f has a boss 55 identical to the boss 52.

Figure 17:
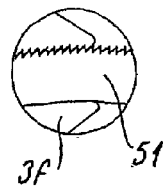
FIG. 17 is a detail of FIG. 16.

As is shown in FIGS. 16 and 17, the catches of the tab 51 engage with the catches of the cavity 54 and are locked with these so as to ensure connection of the two ends of the band 3 to one another. The bosses 52 and 55 allow attachment of a tool to permit sliding of the tab 51 in the cavity 54.

As will be apparent from the foregoing, the invention affords a decisive improvement to the prior art, by providing a gastric ring which is largely nonaggressive with respect to the wall of the stomach, is easy to place on the patient's stomach, and does not require removal after treatment.

A particular advantage of this ring is that it makes it possible to preserve the fibrosis which forms naturally around the band 3, this fibrosis generating scar contraction of the stomach wall, which means there is no need to use an inflatable pouch to adjust the cross section of the opening of the ring.

The gradual tissue integration of the band secures the ring to the wall of the stomach, completely prevents migration ("slippage") of the ring, and provides a wide surface area of contact between the tissues and the band, thus promoting absorption of said band.

The invention claimed is:

1. A gastric ring for treatment of obesity, comprising:
a band which is configured to form a ring around the wall of the stomach, the band including first and second lateral portions and a central portion therebetween, wherein the first and second lateral portions extend radially and outwardly from the ring formed by the central portion, the first and second lateral portions extending from the central portion in juxtaposed contacting relation when the gastric ring is placed on a patient's stomach, and
a fastener including a first member movably connected to a second member such that the fastener is repositionable between an open position and a closed position in which the band can be maintained in the form of said ring;
characterized in that the band is made of at least one bioabsorbable or biodegradable material and has a face intended to come into contact with the wall of the stomach.

2. The gastric ring as claimed in claim 1, wherein at least the face of the band intended to come into contact with the wall of the stomach has a smooth coating for separating this face and this wall at least temporarily.

3. The gastric ring as claimed in claim 2, wherein said coating is made of a bioabsorbable or biodegradable material, in particular a crosslinked collagen material.

4. The gastric ring as claimed in claim 1, wherein the fastener comprises at least one bioabsorbable or biodegradable material.

5. The gastric ring for treatment of obesity as claimed in claim 1,
wherein the band is of such a thickness that it has a flexibility allowing it to be curved transversely with respect to its longitudinal direction, and in that said fastener further includes the first and second lateral portions of the band which continue the central portion of the band intended to surround the patient's stomach and are designed for placing said lateral portions of the band in a substantially radial direction with respect to the circle formed by the central portions of the band when the ring is placed on the stomach of a patient, these lateral portions protruding outward from this circle.

6. The gastric ring as claimed in claim 5, wherein the first and second members of the fastener are configured to engage with said lateral portions of the band.

7. The gastric ring for treatment of obesity as claimed in claim 1,
wherein the band is of such a thickness that it has a rigidity preventing its being curved transversely with respect to its longitudinal direction.

8. The gastric ring as claimed in claim 7, wherein the band is in at least two parts connected pivotably to one another, allowing this band to be placed in an elongate shape so that this band can be introduced into the patient's body using minimally invasive surgical techniques such as celioscopy or laparoscopy.

9. The gastric ring as claimed in claim 8, wherein the band comprises a plurality of "links" connected pivotably to one another.

10. The gastric ring for treatment of obesity as claimed in claim 2,
wherein the band is of such a thickness that it has a flexibility allowing it to be curved transversely with respect to its longitudinal direction, and in that said fastener further includes the first and second lateral portions of the band which continue the central portion of the band intended to surround the patient's stomach and are designed for placing said lateral portions of the band in a substantially radial direction with respect to the circle formed by the central portion of the band when the ring is placed on the stomach of a patient, these lateral portions protruding outward from this circle.

11. The gastric ring for treatment of obesity as claimed in claim 3,
wherein the band is of such a thickness that it has a flexibility allowing it to be curved transversely with respect to its longitudinal direction, and in that said fastener further includes the first and second lateral portions of the band which continue the central portion of the band intended to surround the patient's stomach and are designed for placing said lateral portions of the band in a substantially radial direction with respect to the circle formed by the central portion of the band when the ring is placed on the stomach of a patient, these lateral portions protruding outward from this circle.

12. The gastric ring for treatment of obesity as claimed in claim 4,
wherein the band is of such a thickness that it has a flexibility allowing it to be curved transversely with respect to its longitudinal direction, and in that said fastener further includes the first and second lateral portions of the band which continue the central portion of the band intended to surround the patient's stomach and are designed for placing said lateral portions of the band in a substantially radial direction with respect to the circle formed by the central portion of the band when the ring is placed on the stomach of a patient, these lateral portions protruding outward from this circle.

13. The gastric ring for treatment of obesity as claimed in claim 2,
wherein the band is of such a thickness that it has a rigidity preventing its being curved transversely with respect to its longitudinal direction.

14. The gastric ring for treatment of obesity as claimed in claim 3,
wherein the band is of such a thickness that it has a rigidity preventing its being curved transversely with respect to its longitudinal direction.

15. The gastric ring for treatment of obesity as claimed in claim 4,
wherein the band is of such a thickness that it has a rigidity preventing its being curved transversely with respect to its longitudinal direction.

16. A gastric ring for treatment of obesity, comprising:
a band which is configured to form a ring around the wall of the stomach, the band including first and second lateral portions and a central portion therebetween, wherein the first and second lateral portions extend radially and outwardly from the ring formed by the central portion, the first and second lateral portions extending from the central portion in juxtaposed contacting relation when the gastric ring is placed on a patient's stomach, and
a fastener including a first member movably connected to a second member such that the fastener is repositionable between an open position and a closed position in which the band can be maintained in the form of said ring.

17. The gastric ring for treatment of obesity as in claim 1, wherein the first and second lateral portions extend from the central portion in substantially orthogonal relation.

18. The gastric ring for treatment of obesity as in claim 6, wherein the first member of the fastener is pivotally connected to the second member of the fastener, wherein the lateral portions of the band are freely movable between the first and second members of the fastener when the fastener is in the open position, and wherein movement of the lateral portions of the band between the first and second members of the fastener is inhibited when the fastener is in the closed position.

19. The gastric ring for treatment of obesity as in claim 18, wherein the fastener is configured such that the lateral portions of the band are engaged by the first and second members when the fastener is in the closed position such that the lateral portions are slidable therebetween in frictional relation.

20. The gastric ring for treatment of obesity as in claim 18, wherein the fastener is configured such that the lateral portions are engaged by the first and second members in fixed relation when the fastener is in the closed position such that movement of the lateral portions between the first and second members is prevented.

21. The gastric ring for treatment of obesity as in claim 18, wherein the fastener further includes locking structure to selectively maintain the position of the first and second members.

22. The gastric ring for treatment of obesity as in claim 1, wherein the first and second lateral portions extend linearly from the central portion.

23. The gastric ring for treatment of obesity as in claim 1, wherein the first member of the fastener is pivotably connected to the second member of the fastener at a hinge member.

24. The gastric ring for treatment of obesity as in claim 16, wherein the first member of the fastener is pivotably connected to the second member of the fastener at a hinge member.

* * * * *